(12) United States Patent
Mehta et al.

(10) Patent No.: US 6,783,991 B1
(45) Date of Patent: Aug. 31, 2004

(54) REVERSIBLE AND REUSABLE AUTHENTICATION SYSTEM FOR SECURE DOCUMENTS

(75) Inventors: Rajendra Mehta, Dayton, OH (US); Steven L. Yeager, Dayton, OH (US)

(73) Assignee: The Standard Register Company, Dayton, OH (US)

( * ) Notice: Subject to any disclaimer, the term of this patent is extended or adjusted under 35 U.S.C. 154(b) by 207 days.

(21) Appl. No.: 10/068,516

(22) Filed: Feb. 6, 2002

(51) Int. Cl.[7] .......................... G01N 21/80; G01N 31/22
(52) U.S. Cl. .................. 436/164; 436/163; 422/55; 422/75
(58) Field of Search ................................. 436/163, 164, 436/166; 422/75, 55

(56) References Cited

U.S. PATENT DOCUMENTS

| | | | |
|---|---|---|---|
| 2,333,979 A | | 11/1943 | Brandt |
| 2,445,586 A | * | 7/1948 | Simons ................. 503/202 |
| 3,523,866 A | * | 8/1970 | Krueger et al. ........... 162/140 |
| 4,037,007 A | * | 7/1977 | Wood ...................... 503/204 |
| 4,111,702 A | | 9/1978 | Fraik |
| 4,136,229 A | * | 1/1979 | Godet et al. ............. 162/140 |
| 4,188,431 A | | 2/1980 | Sokol et al. |
| 4,198,445 A | | 4/1980 | Sokol et al. |
| 4,322,466 A | | 3/1982 | Tomlinson |
| 4,725,497 A | | 2/1988 | Honnorat et al. |
| 5,123,999 A | * | 6/1992 | Honnorat et al. ......... 162/140 |
| 5,139,572 A | | 8/1992 | Kawashima |
| 5,188,871 A | | 2/1993 | Collings |
| 5,196,243 A | | 3/1993 | Kawashima |
| 5,215,956 A | | 6/1993 | Kawashima |
| 5,261,954 A | | 11/1993 | Collings |
| 5,264,081 A | | 11/1993 | Honnorat et al. |
| 5,286,061 A | | 2/1994 | Behm |
| 5,354,723 A | | 10/1994 | Gundjian et al. |
| 5,368,334 A | | 11/1994 | Christy et al. |
| 5,421,869 A | | 6/1995 | Gundjian et al. |
| 5,443,629 A | | 8/1995 | Saville et al. |
| 5,478,382 A | | 12/1995 | Miller et al. |
| 5,485,792 A | | 1/1996 | Keyser et al. |
| 5,503,665 A | | 4/1996 | Miller et al. |
| 5,516,362 A | | 5/1996 | Gundjian et al. |
| 5,569,637 A | * | 10/1996 | Cregg ...................... 503/201 |
| 5,595,590 A | | 1/1997 | Belding et al. |
| 5,630,869 A | | 5/1997 | Amon et al. |
| 5,636,874 A | | 6/1997 | Singer |
| 5,698,296 A | * | 12/1997 | Dotson et al. ............ 428/195.1 |
| 5,718,456 A | | 2/1998 | Detwiler, II et al. |
| 5,786,509 A | | 7/1998 | Belding et al. |
| 5,912,205 A | * | 6/1999 | Lakes et al. ............. 503/207 |
| 5,941,572 A | | 8/1999 | Gundjian et al. |
| 6,019,872 A | | 2/2000 | Kurrle |
| 6,035,914 A | * | 3/2000 | Ramsey et al. ........... 156/378 |
| 6,054,021 A | | 4/2000 | Kurrle et al. |
| 6,060,108 A | | 5/2000 | Burd et al. |
| 6,086,966 A | | 7/2000 | Gundjian et al. |
| 6,114,281 A | | 9/2000 | Belding et al. |
| 6,214,766 B1 | | 4/2001 | Kurrle |
| 6,413,305 B1 | * | 7/2002 | Mehta et al. ............. 106/31.41 |
| 6,444,377 B1 | * | 9/2002 | Jotcham et al. ........... 430/10 |
| 6,596,354 B1 | * | 7/2003 | Longdon et al. .......... 428/29 |

FOREIGN PATENT DOCUMENTS

| | | | |
|---|---|---|---|
| FR | 2365656 | * | 5/1978 |
| FR | 2410702 | * | 8/1979 |
| FR | 2539533 | * | 7/1984 |
| GB | 1507454 | * | 4/1978 |
| GB | 2052587 | * | 1/1981 |
| GB | 2321471 | * | 7/1998 |

* cited by examiner

Primary Examiner—Maureen M. Wallenhorst
(74) Attorney, Agent, or Firm—Dinsmore & Shohl LLP

(57) ABSTRACT

The invention is a method and system that is useful to authenticate security paper. Specifically, the present invention relates to a method and system that allows security paper to be authenticated more than once without destroying the authentication mechanism. An authenticating solution is applied to a surface of an authentic document or other authentic security paper. Subsequent application of an activating solution to a surface of a document containing the authenticating solution causes a reversible color change allowing the document to be authenticated.

46 Claims, No Drawings

REVERSIBLE AND REUSABLE AUTHENTICATION SYSTEM FOR SECURE DOCUMENTS

BACKGROUND OF THE INVENTION

The present invention relates to a method and system that is useful to authenticate security paper. Specifically, the present invention relates to a method and system that allows security paper to be authenticated more than once without destroying the authentication mechanism.

Certain types of documents are potentially liable to attempts at counterfeiting. Such documents include checks, travelers' checks, money orders, bankers drafts, bearer bonds, share certificates, stamps, postal orders, and lottery tickets. Many methods exist that allow verification of the authenticity of these types of documents by the person to whom the document might be presented, in order to make the documents secure. For example, one method involves printing an image such as a multiplicity of dots on paper using a starch containing solution and developing the image with an iodine solution. Such a method is disclosed in U.S. Pat. No. 6,214,766 to Kurrle. The starch solution is colorless until exposed to the iodine. However, once the iodine solution has been applied, the printed image is irreversibly revealed.

Another method for authenticating documents involves printing the document with ink that responds to a change in temperature or pressure. U.S. Pat. No. 5,636,874 to Singer teaches once such method. In Singer, the document is printed with thermochromic ink that responds to a change in temperature over an image of a similar color. The thermochromic ink is activated by heat, such as by rubbing, and the ink changes from colored to colorless revealing the printed image underneath. Once the heat is removed, the ink will regain its color. However, the ink can prematurely change color when exposed to a heat source such as being left in a car or being copied on a photo copier. Additionally, the ink can degrade over time, and the degradation can render the security feature useless.

Systems that utilize ultraviolet light also appear in the prior art. One such system is taught by U.S. Pat. No. 5,421,869 to Gundijian et al. The Gundijian system utilizes a substrate that has a first marking fluid applied to it that is invisible to the human eye under both visible and ultraviolet light. A second marking fluid is then applied that causes a reaction with the first marking fluid. The reaction produces fluorescence that is only visible under ultraviolet light. A drawback to this system is the requirement of an ultraviolet light source for verification of authenticity.

Thus, there is a need for a method and system of making a document secure wherein the authentication procedure does not mar the document, the procedure is repeatable, and the procedure does not require costly equipment, and for a document for use in such a method and system in which the document is durable and unchanged by authentication.

SUMMARY OF THE INVENTION

This need is met by the present invention wherein a method and system for authenticating a document is disclosed. The method and system allow the authentication process to be performed numerous times without degradation. The authentication method does not stain or mar the paper.

In accordance with one embodiment of the present invention, a method for authenticating security paper is provided. The method comprises placing an authenticating solution comprising an acid-base indicator in non-ionic form on at least one surface of the security paper and applying an activating solution to the surface containing the authenticating solution. The authenticating solution has an original pH. The activating solution comprises an acid or base that is selected to produce a characteristic color change of the acid-base indicator. The color change only lasts until the activating solution dries. Once this drying occurs, the color change is no longer visible. Typically, the acid-base indicator is selected to be colorless at the original pH of the authenticating solution.

The acid-base indicator may be selected from phenolphthalein, thymolphthalein, fluorescein, α-naptholphthalein and o-cresophthalein and combinations thereof. The concentration of the acid-base indicator is generally less than about 15 percent by weight, and more typically is less than about 5 percent by weight. If one of these indicators is selected, the activating solution may further comprise water as a carrier and a base to cause the desired pH change. The base may be selected from isopropylamine, ethylaamine, diethylamine, butylamine, 3-methoxy propylamine and ammonia and combinations thereof. The concentration of the base selected from this group will generally be in the range of 0.5 to 5 percent by weight. The base may also be selected from sodium hydroxide, potassium hydroxide and ammonia or combinations thereof. The concentration of sodium hydroxide or potassium hydroxide is less than about 0.5 percent by weight, and the concentration of ammonia is less than about 5 percent 5 by weight.

The authenticating solution may be placed on the security paper by printing. The authenticating solution may be printed on the security paper in such a way as to form an invisible image that becomes visible only when the activating solution is applied. Alternatively, the authenticating solution may be printed on the security paper to form a spot coating or a full document flood coating. The printing may comprise flexographic printing. The authenticating solution may further comprise a toner receptive component. The toner receptive component may comprise a toner receptive polymer, and the toner receptive polymer may be selected from styrene-acrylic polymers, acrylic polymers, styrene-butadiene polymers, polyurethane polymers, starch grafted polymers and combinations thereof. The toner receptive polymer may be selected from a styrene-acrylic with a Tg of about 15° C. to about 50° C. and an acid number of about 25 to about 75, and the authenticating solution may be placed on the security paper by flexographic printing. The toner receptive component may be a resin, and the resin may comprise a maleated phenolic modified resin. The authenticating solution may further comprise an oil when the toner receptive component is a resin and may be printed on the security paper by letterpress printing. The activating solution may be contained in a pen and applied to the security paper by marking with the pen to cause the color change of the authenticating solution.

In accordance with another embodiment of the present invention, a security paper authenticating system is provided. The system comprises a security paper having an authenticating solution on at least one surface of the security paper and an activating solution. The authenticating solution comprises an acid-base indicator in non-ionic form and has an original pH. The activating solution comprises as acid or base, and, on applying the activating solution to the security paper, a color change occurs that reverses when the activating solution dries. The acid or base of the activating solution is selected to produce the characteristic color change of the acid-base indicator in the authenticating solution.

Generally, the acid-base indicator is colorless at the original pH of the authenticating solution, The acid-base indicator may be selected from phenolphthalein, thymolphthalein, fluorescein, α-naptholphthalein and o-cresophthalein and combinations thereof. The concentration of the acid-base indicator may be less than about 15 percent by weight and is more typically less than about 5 percent by weight. When the acid-base indicator is selected from such a group, the activating solution may further comprise water as a carrier and a base. The base may be selected from isopropylamine, ethylamine, diethylamine, butylamine, 3-methoxy propylamine and ammonia, and the base will generally have a concentration in the range of 0.5 to 5 percent by weight. Alternatively the base may be selected from sodium hydroxide, potassium hydroxide and ammonia and combinations thereof The concentration of sodium hydroxide or potassium hydroxide may be less than about 0.5 percent by weight and the concentration of ammonia may be less than about 5 percent by weight.

The authenticating solution may be placed on the security paper by printing. The printing may comprise flexographic printing. The authenticating solution may form an invisible image on the surface of the security paper. Alternatively, the authenticating solution may form a spot coating or fill document flood coating on the surface of the security paper. The authenticating solution may further comprise a toner receptive component. The toner receptive component may comprise a toner receptive polymer, and the toner receptive polymer may be selected from styrene-acrylic polymers, acrylic polymers, styrene-butadiene polymers, polyurethane polymers, starch grafted polymers and combinations thereof. The toner receptive polymer may be selected from a styrene-acrylic with a Tg of about 15° C. to about 50° C. and an acid number of about 25 to about 75. The authenticating solution with a toner receptive polymer may be placed on the security paper by flexographic printing. The toner receptive component may be a resin, and the resin may comprise a maleated phenolic modified resin. The authenticating solution may further comprise an oil when the toner receptive component is a resin and the authenticating solution may be printed on the security paper by letterpress printing. The activating solution may be contained in a pen and may be applied to the security paper by marking with the pen.

Accordingly, it is an object of the present invention to provide a method and system of authenticating a document that is reversible and reusable. A further object of the present invention is to provide a system and method of authenticating a document that does not leave a mark on the document. Other objects of the present invention will be apparent in light of the description of the invention embodied herein.

DETAILED DESCRIPTION OF THE PREFERRED EMBODIMENTS

The present invention provides a repeatable, reversible and reliable method and system for authenticating documents. The security paper of the present invention provides a cost effective means of ensuring the security and authenticity of a document.

In general, the present invention involves the use of an authenticating solution placed on security paper. For the purposes of defining and describing the present invention, it is noted that security paper comprises paper substrates, such as those commonly used for checks, money orders. bearer bonds, stamps, postal orders, lottery tickets and the like, and plastic substrates, such as polyolefin, polyester, polyvinyl, polyethlene, and polypropylene products. Typically, the security paper will comprise a paper substrate. The authenticating solution comprises an acid-base indicator that is typically selected to be colorless at the original pH of the authenticating solution. The acid-base indicator generally must be in non-ionic form on the security paper. An activating solution is then applied to the security paper surface containing the authenticating solution. The activating solution comprises an acid or a base selected to produce a characteristic color change of the acid-base indicator when the activating solution causes a change in pH. The color change is visible until the activating solution dries at which time the color change reverses.

The acid-base indicator of the authenticating solution is typically in non-ionic form after the authenticating solution is applied to the security paper. The application of the activating solution causes the acid-base indicator to become ionic and produce a color change in response to the change in pH caused by the application of the acid or a base in the activating solution. Once the activating solution evaporates or dries, the acid-base indicator reverts to its non-ionic form and the color caused by the change in pH reverses. If desired, the activating solution may be applied repeatedly to produce the same reversible color change. This mechanism allows the paper to be authenticated numerous times without degradation of the authentication mechanism and without marring the appearance of the paper. Generally, the color change will generally last for less than about 30 seconds to 1 minute before fading. However, longer times before fading are possible. Typically, the color change reverses within a short period to ensure that the document can be authenticated again quickly, if desired.

The acid-base indicator in the authenticating solution may be any acid-base indicator. However, the acid-base indicator will typically be selected to be colorless at the original pH of the authenticating solution. The selection of such a colorless indicator allows the authenticating solution to be invisible until the activating solution is applied. However, an acid-base indicator that has a color at the original pH of the authenticating solution may also be used. The acid-base indicator will typically be, but is not limited to, phenolphthalein, thymolphthalein, fluorescein, o-cresophthalein and α-naptholphthalein, and combinations thereof. These indicators are colorless at low or acidic pH and exhibit a color change at a high or basic pH. Thus, the indicators are basic indicators. The indicators in this group provide a color change that rapidly reverses when the activating solution dries. Generally, the acid-base indicator will have a concentration of less than about 15 percent by weight of the authenticating solution. More typically, the indicators will have a concentration of less than 5 percent by weight in the authenticating solution.

The authenticating solution does not require the presence of an additional acid or base in the authenticating solution to improve the maintenance of the indicator in its colorless state by acting as a buffer. The indicator will maintain its colorlessness when the activating solution dries even after repeated applications of the activating solution.

The authenticating solution can further comprise a number of binders into which the acid-base indicator is incorporated to improve adhesion of the solution to the substrate. Resins and polymers may be used as binders. For example, a styrene acrylic binder or styrene butadiene binder may be used. Polyvinyl alcohol, polyvinyl pyrollidone and sodium carboxymethylcellulose may also be used. Water-based polymer emulsions can act as a binder. Starch binders and latex based binders may be used. Even solvent based or 100 percent solids systems such as UV curable systems can be incorporated into the authenticating solution. However, the authenticating solution will generally be water-based.

The authenticating solution is typically placed on the paper substrate by printing. Printing may be accomplished with flexographic printing techniques or gravure printing. The authenticating solution may be printed to form an indicia, spot coating or full document flood coating. A spot coating covers only a portion of the paper substrate. A flood coating covers the entire surface of the substrate, and this may be used, as well. The authenticating solution may also be applied to the paper substrate by other techniques, such as by coating or spraying. For example, a mask or stencil with voids arranged to form a logo or other indicia could be used during a spraying operation to mask part of the paper so that the logo or other indicia was invisibly applied to the paper. The pH of the paper substrate does not affect the authentication system and method. The pH typically associated with paper does not cause a color change of the authenticating solution or necessitate the selection of a specific acid-base indicator. Similarly, a different acid or base in the activating solution is not required due to the pH of the paper. Therefore, the authentication method and system may be used in conjunction with any type of paper substrate, and the authentication method and system is widely and easily applicable to all types of documents that may be secured regardless of the type of paper used for the document.

The authenticating solution may also be incorporated into a toner receptive coating to give evidence of tampering. Such a toner receptive coating makes the removal of subsequently applied toner, such as printer ink, extremely difficult. A document with the toner receptive authenticating coating could be run through a laser printer. If someone attempted to remove the toner, the toner could not be readily removed in the areas with the coating. Additionally, the presence of the coating could be confirmed by applying the activating solution. The toner receptive coating may be mainly comprised of a toner receptive polymer emulsion. One example of a polymer useful for the toner receptive polymer emulsion is a styrene-acrylic with a Tg in the range of 15° C. to 50° C. and an acid number of 25 to 75. Examples of such a styrene-acrylic include Joncryl 77 (S.C. Johnson Polymer, Sturtevant, Wis.) and Carboset Ga. 2137 (B.F. Goodrich Specialty Chemicals, Clevland, Ohio). Other types of polymers may also be used such as acrylics, styrene-butadiene, polyurethane, and starch grafted polymers. Other components of the toner receptive coating may be water, an acid or base for pH control, a crosslinker, fluorescent dye, defoamer, surfactant/wetting agent and filler.

The indicator in an authenticating solution that is applied by flexographic or gravure printing is generally dispersed in the authenticating solution. Therefore, the indicator is generally in solid form on the security paper once the authenticating solution has dried. The indicator is also in a non-ionic form once it has been applied to the security paper. The application of activating solution causes the indicator to dissolve and the color change to occur as the indicator changes from a non-ionic to ionic form. Once the activating solution dries, the indicator reverts to its solid form and non-ionic form, and the color change reverses.

The authenticating solution may further be incorporated into a toner receptive coating that may be printed by letterpress printing to form a spot coating or a flood coating. The letterpress toner receptive coating comprises a resin, an oil to dissolve the resin, and an acid-base indicator. The resin is used to control toner adhesion. The resin may comprise rosin esters, terpenes, terpene phenolics, aliphatic hydrocarbon resins, aromatic hydrocarbon resins, coumarine indenes and pure monomer resins. SPR 10 (Akzo Nobel), a maleated phenolic modified resin, Kristalex 3100 (Hercules, Inc., Wilmington, Del.), Piccotex 120 (Hercules, Inc., Wilmington, Del.) and Resinall 434 (Resinall, Inc., Samford, Conn.) are generally used. The oil may comprise oils known for use in inks such as naphthenics and aromatics. Sylfat 9012 (Arizona Chemical, Panama City, Fla.), a tall oil fatty acid ester, is generally used. A polar solvent such as hexyl carbitol may be used to dissolve the acid-base indicator. The indicator is dissolved into the oil/resin blend at a high temperature, and the indicator does not have to remain fully in solution to be active. Other components of the letterpress toner receptive coating may include UV absorbers, hindered amine light stabilizers, antioxidants, fillers and rheology modifiers.

The indicator in an authenticating solution that is applied by letterpress printing is generally in solution. The ink applied by letterpress printing is absorbed into the fibers of the security paper, but it rarely completely dries. Therefore, the indicator is not generally in solid form on the security paper when the authenticating solution is applied by letterpress printing. The application of the activating solution to the security paper causes the indicator to change from a non-ionic to an ionic form producing a color change. Once the activating solution evaporates, the indicator reverts to its non-ionic form, and the color change reverses. Because the acid-base indicator is generally selected to be colorless at the original pH of the authenticating solution, the authenticating solution will have color only for a short time when exposed to the activating solution. Therefore, the document is not marked or marred by the present authenticating method because the authenticating solution returns to its colorless state after the activating solution dries. This lack of marking or marring of the paper is desirable because the document is not altered by the authentication, and there is no danger of information on the document being obscured by the authentication mechanism.

The activating solution may comprise any acid or base that is selected to produce the characteristic color change of the acid-base indicator incorporated into the authentication solution. The concentration of the acid or base must be carefully selected to produce the desired color change that reverses itself. If the concentration of acid or base used in the activating solution is too strong, the color change can be permanent which is not desirable. Conversely, if the concentration of acid or base is too weak, no color change will occur, and the document cannot be authenticated.

When basic indicators are used the activating solution may comprise water as a carrier and a base. The base may comprise sodium hydroxide or potassium hydroxide and ammonia as a base. For such an activating solution, the concentration of water is typically between 94.5 to 99.5 percent. The concentration of sodium hydroxide or potassium hydroxide is typically 0.005 to 0.5 percent, and the concentration of ammonia, in a solution of about 26 percent ammonia, is about 0.5 and 5 percent. These concentrations ensure that the acid-base indicator dissolves in the activating solution, exhibits the appropriate color change and reverts to colorless when the activating solution carrier dries. Typically, the base will be selected from the group comprising isopropylamine, ethylamine, diethylamine, butylamine, 3-methoxy propylamine or ammonia and combinations thereof. These bases generally have a concentration in the range of about 0.5 to 5 percent, and the activating solution will further comprise water as a carrier. Generally, the activating solution comprising isopropylamine and water will provide the color change that will reverse most easily and provide the best repeatability.

The activating solution may be contained in a pen and applied to the paper substrate by marking with the pen. Such a pen may have a polyester or acryl tip, for example. The activating solution may also be applied to the paper substrate by using a container containing the solution that is equipped with a sponge-like applicator at one end of the container. The activating solution may also be sprayed on, brushed on or rolled on. The general requirement is that the authenticating solution is contained on or in the paper substrate and the activating solution be applied to the paper. The activating solution may not be placed or printed on the paper and the authenticating solution applied to the paper via a mechanism such as a pen. The authentication mechanism is not affected by the use of a traditional pH pen on the paper.

EXAMPLE 1

A water-based authentication solution of polyvinyl alcohol (PVA), polyvinyl pyrollidone (PVP) and sodium carboxymethylcellulose (CMC) was prepared using a phenolphthalein indicator. The authentication solution was coated onto paper using a #6 meyer rod. Several activating solutions were tested. A mild ammonia solution was very effective at producing a reversible color change when swiped onto the coated paper using a cotton swab. A sodium hydroxide solution and ammonia solution was also tested. A concentration of 0.02% sodium hydroxide provided the best reversible color change. The composition of the authenticating solution and the activating solutions tested is shown below. Percentages are shown by weight. The concentrations in parentheses are possible concentration ranges.

| Authenticating Solution | |
|---|---|
| Water | 68.90% (40–80) |
| PVA - Airvol 21–205 (Air Products, Allentown, PA) | 21.17% (5–35) |
| PVP - PVP K-30 (ISP Technologies Inc., Wayne, NJ) | 1.96% (0.5–10) |
| CMC - Aqualon CMC-T (Hercules Inc., Wilmington, DE) | 3.92% (1–9) |
| Dynol 604 (Air Products, Allentown, PA) | 0.24% (0.1–2.0) |
| Propylene Glycol (Aldrich Chemical Co., Milwaukee, WI) | 0.98% (0.3–2.0) |
| Silwet L-77 (OSi Specialties, Dansbury, CT) | 0.24% (0.1–1.0) |
| Amical Flowable (biocide) (Angus Chemical Co., Buffalo Grove, IL) | 0.09% (0.05–0.4) |
| Phenolphthalein Base Indicator (Aldrich Chemical Co., Milwaukee, WI) | 2.50% (0.5–8) |
| Activating Solution | |
| Water | 97.98% (94.5–99.5) |
| Sodium Hydroxide | 0.02% (0.005–0.5) |
| Ammonia Solution (~26%) | 2.00% (0.5–5.0) |

Thymolphthalein, fluorescein, α-naptholphthalein and o-cresolphthalein may all be substituted for phenolphthalein as the base indicator in this system.

EXAMPLE 2

| Authenticating Solution | |
|---|---|
| Water | 34.00% (25–40) |
| Urea (Aldrich Chemical Co., Milwaukee, WI) | 25.00% (10–30) |
| Polyviol LL603, 20% Solution (Wacker Chemicals, Norwalk, CT) | 25.00% (10–40) |
| PenCP 318 (Penford Products, Cedar Rapids, IA) | 12.50% (5–25) |
| o-Cresolphthalein (Aldrich Chemical Co., Milwaukee, WI) | 2.50% (1–10) |
| Silwet L-77 (OSi Specialties, Danbury, CT) | 0.50% (0.1–1.0) |
| SE 23 (Wacker Silicones, Adrian, MI) | 0.50% (0.1–2.0) |
| Activating Solution | |
| Water | 98% (95–99.5) |
| Isopropylamine (Aldrich Chemical Co., Milwaukee, WI) | 2% (0.5–5) |

A system comprised of the above components performs the functions of the invention especially well.

EXAMPLE 3

A toner receptive coating formula incorporating an authenticating solution may have the formula shown below.

| Authenticating Solution | |
|---|---|
| Styrene-Acrylic Polymer Emulsion (S. C. Johnson Polymer, Sturtevant, WI) | 86.61% (60–90) |
| Water | 6.88% (5–25) |
| Ammonia (Aldrich Chemical Co., Milwaukee, WI) | 0.02% (0.01–0.1) |
| Zinc Oxide, Crosslinker (S. C. Johnson Polymer, Sturtevant, WI) | 3.49% (1–5) |
| Tinopal SCP, UV Dye (Ciba-Geigy, Tarrytown, NY) | 0.25% (0.1–0.5) |
| Foamburst 338, Defoamer (Ross Chemical, Fountain Inn, SC) | 0.25% (0.1–0.5) |
| o-Cresolphthalein (Aldrich Chemical Co., Milwaukee, WI) | 2.50% (1–15) |

EXAMPLE 4

A letterpress toner receptive coating may have the formula shown below.

| Authenticating Solution | |
|---|---|
| SPR 10 (Akzo Nobel Resins, Woodstock, CT) | 50.7% (35–55) |
| Sylfat 9012 (Arizona Chemical, Panama City, FL) | 46.8% (20–55) |
| o-Cresolphthalein (Sigma-Aldrich Chemical, Milwaukee, WI) | 2.5% (0.5–5) |

EXAMPLE 5

A letterpress toner receptive coating may have the formula shown below.

| Authenticating Solution | |
|---|---|
| SPR 10 (Akzo Nobel Resins, Woodstock, CT) | 39.86% (35–55) |
| Sylfat 9012 (Arizona Chemical, Panama City, FL) | 48.38% (20–55) |

-continued

| Authenticating Solution | |
|---|---|
| o-Cresolphthalein (Sigma-Aldrich Chemical, Milwaukee, WI) | 4.09% (0.5–5) |
| Aerosil R972 (Degussa Corp., Ridgefield Park, NJ) (rheology modifier) | 4.26% (2–7) |
| Tinuvin 5055 (Ciba Specialty Chemicals, Tarrytown, NY) (UV Stabilizer) | 3.41% (1–6) |

EXAMPLE 6

A letterpress toner receptive coating may have the formula shown below and performs the functions of the invention especially well.

| Authenticating Solution | |
|---|---|
| Hexyl Carbitol (Van Waters & Rogers, Kirkland, WA) | 17.15% (5–20) |
| SPR 10 (Akzo Nobel Resins, Woodstock, CT) | 40.14% (35–55) |
| Sylfat 9012 (Arizona Chemical, Panama City, FL) | 30.70% (20–55) |
| o-Cresolphthalein (Sigma-Aldrich Chemical, Milwaukee, WI) | 3.43% (0.5–5) |
| Aerosil R972 (Degussa Corp., Ridgefield Park, NJ) | 5.15% (2–7) |
| Tinuvin 5055 (Ciba Specialty Chemicals, Tarrytown, NY) | 3.43% (1–6) |

EXAMPLE 7

Activating solutions for use with a toner receptive coating may have the formulas shown below.

| Activating Solution | |
|---|---|
| Water | 98% (95–99.5) |
| Isopropylamine (Sigma-Aldrich Chemical, Milwaukee, WI) | 2% (0.5–5) |
| Water | 98% (95–99) |
| Isoproylamine (Sigma-Aldrich Chemical, Milwaukee, WI) | 0.99% (0.5–2) |
| Ammonia (Chemical Specialties, Dayton, OH) | 1.01% (0.5–3) |

It will be obvious to those skilled in the art that various changes may be made without departing from the scope of the invention, which is not to be considered limited to what is described in the specification.

What is claimed is:

1. A method for authenticating security paper comprising:
   placing an authenticating solution on at least one surface of said security paper, said authenticating solution comprising an acid-base indicator in non-ionic form and having an original pH; and
   applying to said surface of said security paper an activating solution comprising an acid or base selected to produce a characteristic color change of said acid-base indicator and thereby authenticating said security paper, wherein said characteristic color change will disappear when the activating solution dries.

2. The method as claimed in claim 1 wherein said acid-base indicator is colorless at said original pH of said authenticating solution.

3. The method as claimed in claim 1 wherein the concentration of said acid-base indicator is less than about 15 percent by weight.

4. The method as claimed in claim 1 wherein the concentration of said acid-base indicator is less than about 5 percent by weight.

5. The method as claimed in claim 1 wherein said acid-base indicator is selected from phenolphthalein, thymolphthalein, fluorescein, α-naptholphthalein and o-cresophthalein and combinations thereof.

6. The method as claimed in claim 1 wherein said activating solution further comprises water.

7. The method as claimed in claim 6 wherein said base is selected from isopropylamine, ethylamine, diethylamine, butylamine, 3-methoxy propylaimine and ammonia and combinations thereof.

8. The method as claimed in claim 7 wherein the concentration of said base is in the range of about 0.5 to 5 percent by weight.

9. The method as claimed in claim 6 wherein said base is selected from sodium hydroxide, potassium hydroxide and ammonia and combinations thereof.

10. The method as claimed in claim 9 wherein the concentration of said sodium hydroxide or potassium hydroxide is less than about 0.5 percent by weight and the concentration of said ammonia is less than about 5 percent by weight.

11. The method as claimed in claim 1 wherein said authenticating solution is placed on said security paper by printing.

12. The method as claimed in claim 11 wherein said authenticating solution is printed to form an invisible image on said security paper.

13. The method as claimed in claim 11 wherein said authenticating solution is printed to form a spot coating on said security paper.

14. The method as claimed in claim 11 wherein said authenticating solution is printed to form a full document flood coating on said security paper.

15. The method as claimed in claim 11 wherein said printing comprises flexographic printing.

16. The method as claimed in claim 1 wherein said authenticating solution further comprises a toner receptive component comprising a toner receptive polymer.

17. The method as claimed in claim 16 wherein said toner receptive polymer is selected from styrene-acrylic polymers, acrylic polymers, styrene-butadiene polymers, polyurethane polymers, starch grafted polymers and combinations thereof.

18. The method as claimed in claim 16 wherein said toner receptive polymer is selected from a styrene-acrylic with a Tg of about 15° C. to about 50° C. and an acid number of about 25 to about 75.

19. The method as claimed in claim 16 wherein said authenticating solution is placed on said security paper by flexographic printing.

20. The method as claimed in claim 1 wherein said authenticating solution further comprises a toner receptive component comprising a resin and an oil.

21. The method as claimed in claim 20 wherein said resin comprises a maleated phenolic modified resin.

22. The method as claimed in claim 20 wherein said authenticating solution is placed on said security paper by letterpress printing.

23. The method as claimed in claim 1 wherein said activating solution is contained in a pen and is applied to said security paper by marking with said pen.

24. A security paper authenticating system comprising:
   a security paper having an authenticating solution on at least one surface of said security paper, said authenticating solution comprising an acid-base indicator in non-ionic form and having an original pH; and an activating solution comprising an acid or base selected to produce a characteristic color change of said acid-base indicator, wherein on applying the activating solution to said security paper a color change occurs that reverses when said activating solution dries.

25. The system as claimed in claim 24 wherein said acid-base indicator is colorless at said original pH of said authenticating solution.

26. The system as claimed in claim 24 wherein the concentration of said acid-base indicator is less than about 15 percent by weight.

27. The system as claimed in claim 24 wherein the concentration of said acid-base indicator is less than about 5 percent by weight.

28. The system as claimed in claim 24 wherein said acid-base indicator is selected from phenolphthalein, thymolphthalein, fluorescein, α-naptholphthalein and o-cresophthalein and combinations thereof.

29. The system as claimed in claim 24 wherein said activating solution further comprises water as a carrier.

30. The system as claimed in claim 29 wherein said base is selected from isopropylamine, ethylamine, diethylamine, butylamine, 3-methoxy propylamine and ammonia and combinations thereof.

31. The system as claimed in claim 30 wherein said concentration of said base is in the range of 0.5 to 5 percent by weight.

32. The system as claimed in claim 29 wherein said base is selected from sodium hydroxide, potassium hydroxide and ammonia and combinations thereof.

33. The system as claimed in claim 32 wherein the concentration of said sodium hydroxide or potassium hydroxide is less than about 0.5 percent by weight and the concentration of said ammonia is less than about 5 percent by weight.

34. The system as claimed in claim 24 wherein said authenticating solution is placed on said security paper by printing.

35. The system as claimed in claim 34 wherein said printing comprises flexographic printing.

36. The system as claimed in claim 24 wherein said authenticating solution forms an invisible image.

37. The system as claimed in claim 24 wherein said authenticating solution is on said security paper as a spot coating.

38. The system as claimed in claim 24 wherein said authenticating solution is on said security paper as a fill document flood coating.

39. The system as claimed in claim 24 wherein said authenticating solution further comprises a toner receptive component comprising a toner receptive polymer.

40. The system as claimed in claim 39 wherein said toner receptive polymer is selected from styrene-acrylic polymers, acrylic polymers, styrene-butadiene polymers, polyurethane polymers, starch grafted polymers and combinations thereof.

41. The system as claimed in claim 39 wherein said toner receptive polymer is selected from a styrene-acrylic with a Tg of about 15° C. to about 50° C. and an acid number of about 25 to about 75.

42. The system as claimed in claim 39 wherein said authenticating solution is placed on said security paper by flexographic printing.

43. The system as claimed in claim 24 wherein said authenticating solution further comprises a toner receptive component comprising a resin and an oil.

44. The system as claimed in claim 43 wherein said resin comprises a maleated phenolic modified resin.

45. The system as claimed in claim 43 wherein said authenticating solution is placed on said security paper by letterpress printing.

46. The system claimed in claim 24 wherein said activating solution is contained in a pen and is applied to said security paper by marking with said pen.

* * * * *

UNITED STATES PATENT AND TRADEMARK OFFICE
CERTIFICATE OF CORRECTION

PATENT NO. : 6,783,991 B1  Page 1 of 1
APPLICATION NO. : 10/068516
DATED : August 31, 2004
INVENTOR(S) : Mehta et al.

It is certified that error appears in the above-identified patent and that said Letters Patent is hereby corrected as shown below:

Col. 12, line 10 "fill" should read --full--

Signed and Sealed this

Fourth Day of July, 2006

JON W. DUDAS
*Director of the United States Patent and Trademark Office*